(12) United States Patent
Hirose

(10) Patent No.: US 9,131,841 B2
(45) Date of Patent: Sep. 15, 2015

(54) IMAGE ACQUISITION APPARATUS

(75) Inventor: Futoshi Hirose, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 383 days.

(21) Appl. No.: 13/574,873

(22) PCT Filed: Jan. 19, 2011

(86) PCT No.: PCT/JP2011/000264
§ 371 (c)(1),
(2), (4) Date: Jul. 24, 2012

(87) PCT Pub. No.: WO2011/099236
PCT Pub. Date: Aug. 18, 2011

(65) Prior Publication Data
US 2012/0293770 A1   Nov. 22, 2012

(30) Foreign Application Priority Data
Feb. 10, 2010  (JP) .................................. 2010-027251

(51) Int. Cl.
*A61B 3/10* (2006.01)
(52) U.S. Cl.
CPC ............... *A61B 3/1025* (2013.01); *A61B 3/102* (2013.01)
(58) Field of Classification Search
CPC ........ A61B 3/10; A61B 3/102; A61B 3/1025; A61B 3/14; A61B 3/15; A61B 3/156
USPC .................. 351/205, 206, 214–216, 221, 246
See application file for complete search history.

(56) References Cited

U.S. PATENT DOCUMENTS

| 6,769,769 B2 | 8/2004 | Podoleanu et al. |
|---|---|---|
| 7,510,282 B2 | 3/2009 | Ueno et al. |
| 8,308,297 B2 | 11/2012 | Hirose et al. |
| 2004/0036838 A1 | 2/2004 | Podoleanu et al. |

(Continued)

FOREIGN PATENT DOCUMENTS

| CN | 1694644 A | 11/2005 |
|---|---|---|
| DE | 10 2008 000 225 B3 | 3/2009 |

(Continued)

OTHER PUBLICATIONS

R. B. Rosen et al. "Simultaneous OCT/SOL/ICG System", Proc of SPIE, vol. 6079, Feb. 20, 2006 pp. 60790A-1 through 60790A-6.*

(Continued)

*Primary Examiner* — Huy K Mai
(74) *Attorney, Agent, or Firm* — Fitzpatrick, Cella, Harper & Scinto

(57) ABSTRACT

An image acquisition apparatus irradiates light from a light source to an inspection object, obtains a tomographic image of the inspection object on the basis of a combined beam obtained by combining a return beam from the inspection object due to the irradiated light and a reference beam corresponding to the light, and obtains a plane image of the inspection object on the basis of the return beam from the inspection object due to the irradiated light. The apparatus performs a first scanning process to main-scan the irradiated light when the tomographic image is obtained, performs a second scanning process to main-scan the irradiated light at a speed higher than that in the first scanning process when the plane image is obtained, and performs a third scanning process to sub-scan the irradiated light when each of the tomographic image and the plane image is obtained.

28 Claims, 5 Drawing Sheets

(56) References Cited

U.S. PATENT DOCUMENTS

| | | |
|---|---|---|
| 2005/0140984 A1 | 6/2005 | Hitzenberger |
| 2007/0076223 A1 | 4/2007 | Podoleanu et al. |
| 2008/0024721 A1 | 1/2008 | Ueno et al. |
| 2009/0091766 A1 | 4/2009 | Hirose |
| 2009/0285354 A1 | 11/2009 | Hirose et al. |
| 2010/0103374 A1* | 4/2010 | Hirose et al. .................. 351/206 |
| 2010/0321700 A1 | 12/2010 | Hirose et al. |
| 2011/0001927 A1 | 1/2011 | Kasper |
| 2011/0085136 A1 | 4/2011 | Ferguson et al. |
| 2011/0234975 A1 | 9/2011 | Hirose |
| 2011/0273668 A1 | 11/2011 | Hirose |
| 2011/0301455 A1 | 12/2011 | Numajiri et al. |
| 2012/0044455 A1 | 2/2012 | Hirose |
| 2012/0062843 A1 | 3/2012 | Ferguson et al. |

FOREIGN PATENT DOCUMENTS

| | | | |
|---|---|---|---|
| EP | 1 952 755 | A1 | 8/2008 |
| GB | 2 429 522 | A | 2/2007 |
| JP | 11-253403 | A | 9/1999 |
| JP | 2008-029467 | A | 2/2008 |
| JP | 2009-535164 | A | 10/2009 |
| WO | 2004/002298 | A1 | 1/2004 |
| WO | 20041002298 | A1 | 1/2004 |
| WO | 2006/105903 | A2 | 10/2006 |
| WO | 2007/130411 | A2 | 11/2007 |
| WO | 2009/098516 | A2 | 8/2009 |
| WO | 2010/128630 | A1 | 11/2010 |

OTHER PUBLICATIONS

May 6, 2011 International Search Report and Written Opinion in PCT/JP2011/000264.

Aug. 23, 2012 International Preliminary Report on Patentability in International Patent Appln. No. PCT/JP32011/000264.

Apr. 1, 2014 Chinese Official Action in Chinese Patent Appln. No. 201180009145.2.

* cited by examiner

IMAGE ACQUISITION APPARATUS

TECHNICAL FIELD

The invention relates to an image acquisition apparatus for acquiring an image of an inspection object.

BACKGROUND ART

It is desirable to obtain a plane image of an inspection object prior to obtaining a tomographic image by an Optical Coherence Tomography (OCT). An image acquisition range of the OCT can be known by the plane image.

Therefore, such an apparatus that an optical system of the OCT and an optical system of a Scanning Laser Ophthalmoscope (SLO) to obtain the plane image of the inspection object are partially shared has been disclosed in the below-mentioned PTL 1. Such a technique that each of the optical system of the OCT and the optical system of the SLO has a light source for generating light having different oscillating wavelengths and a galvano mirror for main-scanning a measuring beam which is irradiated to the inspection object and a galvano mirror for sub-scanning it are used in common has been disclosed there. A dichroic mirror is used on an optical path adapted to share the optical systems.

Such a technique that the means for main-scanning the measuring beam and the means for sub-scanning it are separately provided for the optical system of the OCT and the optical system of the SLO has been disclosed in the below-mentioned PTL 2. Such a technique that a polygon mirror which can main-scan at a speed higher than that of the galvano mirror is provided for the optical system of the SLO has been disclosed there. In the OCT, since an image acquisition time which is determined by a response time (an exposure time and a transfer time) of a line sensor is later than a scanning speed of the polygon mirror, the galvano mirror is used. Such a technique that the means for sub-scanning is provided for each of the optical system of the OCT and the optical system of the SLO has been disclosed. The dichroic mirror is used on the optical path adapted to share the optical systems.

CITATION LIST

Patent Literature

PTL 1: Japanese Patent Application Laid-Open No. H11-253403
PTL 2: Japanese Patent Application Laid-Open No. 2008-029467

SUMMARY OF INVENTION

Technical Problem

However, since the whole optical system enlarges in size, the above construction is undesirable in consideration of a viewpoint of an occupied area of an ophthalmological apparatus.

Solution to Problem

It is an object of the invention to provide such an image acquisition apparatus which can miniaturize an apparatus in which an optical system of an OCT and an optical system of an SLO are partially shared and can obtain an SLO image of an inspection object at a high speed without being restricted by an image acquisition speed of the OCT.

In order to achieve the object discussed above, the present invention provides with an image acquisition apparatus comprising: an irradiating means for irradiating light from a light source to an inspection object, tomographic image obtaining means for obtaining a tomographic image of the inspection object on the basis of a combined beam obtained by combining a return beam from the inspection object due to the light irradiated by the irradiating means and a reference beam corresponding to the light, plane image obtaining means for obtaining a plane image of the inspection object on the basis of the return beam from the inspection object due to the light irradiated by the irradiating means, first scanning means for main-scanning the light irradiated by the irradiating means when the tomographic image is obtained, second scanning means for main-scanning the light irradiated by the irradiating means at a speed higher than that in the first scanning means when the plane image is obtained, and third scanning means for sub-scanning the light irradiated by the irradiating means when each of the tomographic image and the plane image is obtained.

Advantageous Effects of Invention

According to the image acquisition apparatus of the invention, by using the means for sub-scanning in common for the optical system of the OCT and the optical system of the SLO in consideration of the foregoing problem, the apparatus can be miniaturized. By providing the scanning means of a high main scanning speed for the optical system of the SLO separately from the main-scanning means for the OCT, the SLO image of the inspection object can be obtained at a high speed without being restricted by the image acquisition speed of the OCT.

Further features of the present invention will become apparent from the following description of exemplary embodiments with reference to the attached drawings.

DESCRIPTION OF EMBODIMENTS

Subsequently, embodiments of the invention will be described.

First Embodiment

An optical image acquisition apparatus (also referred to as an image acquisition apparatus) according to the first embodiment can obtain a tomographic image (OCT image) on the basis of a beam obtained by combining a return beam from an inspection object and a reference beam and can obtain a plane image (SLO image) on the basis of the return beam. At this time, the optical image acquisition apparatus in the embodiment is constructed so that a scanner constructing scanning means for scanning a measuring beam is also shared within a range as much as possible in order to miniaturize the apparatus. Although the SLO uses the scanning means for scanning at a high speed, in the OCT, an image acquisition time which is determined by a response time (an exposure time and a transfer time) of a line sensor is later than a scanning speed of a polygon mirror or a resonant scanner. Therefore, an X scanner cannot be shared but is constructed by two individual X scanners (first scanning means and second scanning means) for the image acquisition of an SLO image and an OCT image. A Y scanner (third scanning means) is constructed by one scanner because it is shared for the image acquisition of both of the SLO image and the OCT image.

The X scanner denotes a scanner for scanning the measuring beam in the direction which is perpendicular to the eye axis of the eye to be inspected, that is, the direction (main scanning direction) which is parallel with the paper surface in FIG. 1, which will be described hereinafter. The Y scanner denotes a scanner for scanning the measuring beam in the direction which is perpendicular to the eye axis of the eye to be inspected, that is, the direction (subscanning direction) which is perpendicular to the paper surface in FIG. 1, which will be described hereinafter. Therefore, when the OCT image is acquired, the X scanner (refer to an X scanner 121-1 in FIG. 1) plays a role of the main scan and the Y scanner (refer to a Y scanner 121-3 in FIG. 1) plays a role of the subscan. On the other hand, when the SLO image is acquired, the X scanner (refer to an X scanner 121-2 in FIG. 1) plays a role of the main scan and the Y scanner (refer to the Y scanner 121-3 in FIG. 1) plays a role of the subscan.

The above two X scanners are scanned by different scanning frequencies in the same scanning direction and are arranged optically in parallel. The measuring beam is guided to the inspection object through one of the X scanners.

Subsequently, a construction of the whole optical image acquisition apparatus in the embodiment will be described further in detail by using FIG. 1. An optical image acquisition apparatus 100 in the embodiment constructs a Michelson interferometer as a whole as illustrated in FIG. 1.

Figure 1:
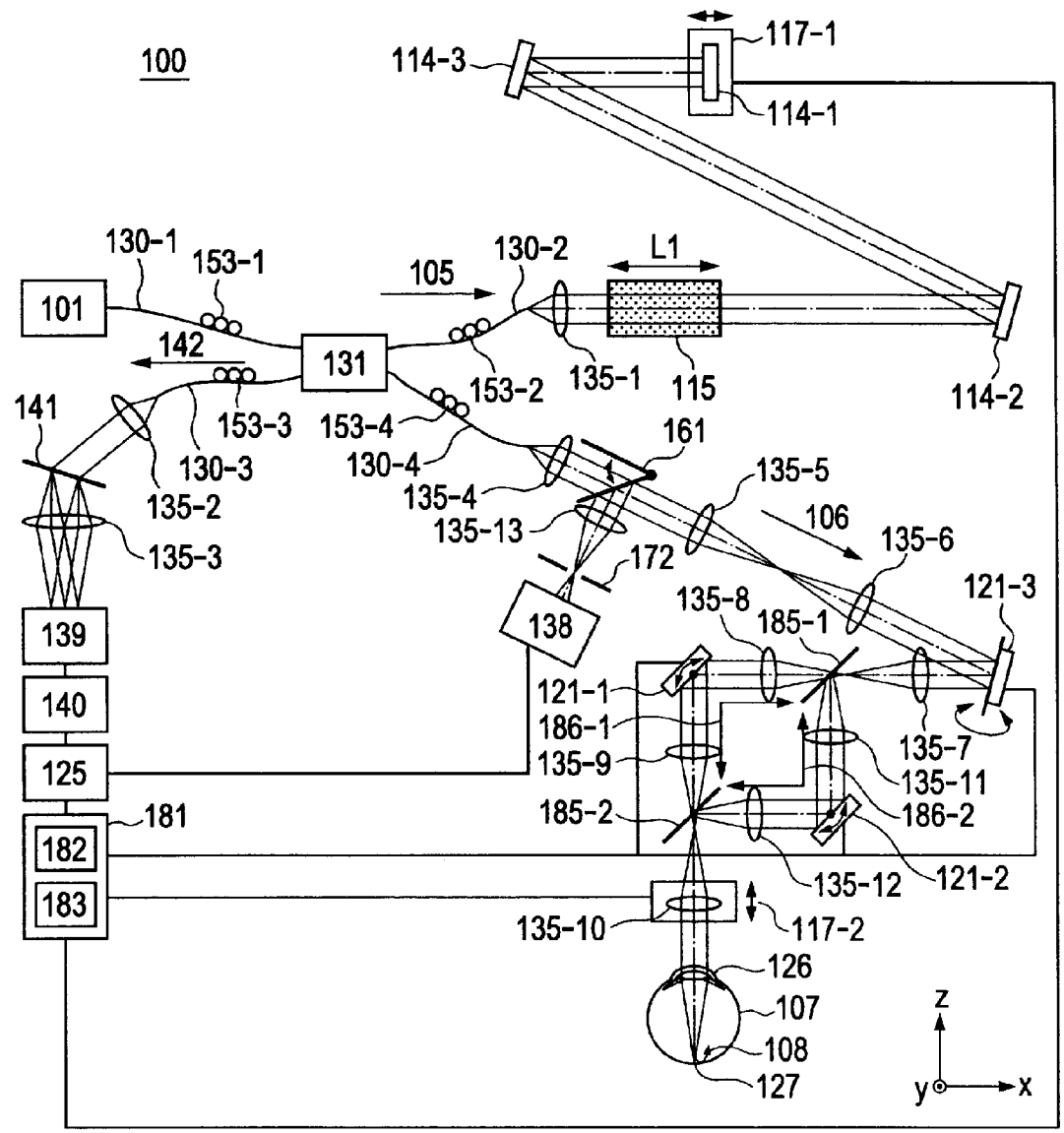
FIG. 1 is a diagram for describing a construction of a whole optical image acquisition apparatus in the first embodiment of the invention.

In FIG. 1, a light source 101 is shared for the image acquisition of the SLO image and the OCT image. An SLD (Super Luminescent Diode) or the like serving as a light source for generating low-coherence light is desirable as a light source. The light emitted from the light source 101 is divided into a reference beam 105 and a measuring beam 106 at a ratio of 90:10 through a single mode fiber 130-1 and a photocoupler 131 (also referred to as first separating means).

Reference numeral 121-1 shown in FIG. 1 denotes the X scanner which plays a role of the main scan when the OCT image is acquired, 121-2 denotes the X scanner which plays a role of the main scan when the SLO image is acquired, and 121-3 denotes the Y scanner which is shared for the image acquisition of the SLO image and the OCT image.

The measuring beam 106 is guided to an eye 107 to be inspected and serving as an inspection object of an observation target through a single mode fiber 130-4, the Y scanner 121-3, one of the X scanners 121-1 and 121-2, lenses 135-5 to 135-12, and the like. Flip mirrors 185-1 and 185-2 have a role of switching optical paths. The measuring beam 106 is returned as a return beam 108 which has been reflected or scattered by the eye 107 to be inspected as an observation target and is combined with the reference beam 105 by the photocoupler 131. Polarization controllers 153-1 to 153-4 adjust a state of polarization of the measuring beam 106 and the reference beam 105.

The reference beam 105 and the return beam 108 are combined and, thereafter, a combined beam is spectro-separated every wavelength by a transmission grating 141 and input to a line camera 139. The line camera 139 converts a light intensity into a voltage every position (wavelength). A tomographic image of the eye 107 to be inspected is constructed by a personal computer 125 by using the obtained voltage signal. Electric stages 117-1 and 117-2, the X scanners 121-1 and 121-2, and the Y scanner 121-3 are controlled and driven by the personal computer 125 through a driver unit 181.

A part of the return beam 108 is input to a detector 138 by a movable beam splitter 161 (also referred to as second separating means which can be inserted or removed at a position in front of the first separating means). The detector 138 converts the light intensity into an electric signal and a plane image of the eye 107 to be inspected is constructed by using the electric signal. When the plane image is obtained, it is necessary to insert the second separating means onto an optical path in order to guide the return beam to the detector 138. However, when the tomographic image is obtained, since it is unnecessary to insert it, the second separating means is removed from the optical path. Thus, when the tomographic image is obtained, a loss of light amount that is caused by the separation of the return beam by the second separating means can be suppressed. In this instance, when the plane image is obtained, the loss of light amount is also caused by the separation of the measuring beam by the second separating means. Therefore, it is desirable that the light amount of the light source at the time of obtaining the plane image is set to be larger than the light amount of the light source at the time of obtaining the tomographic image.

Subsequently, a construction around the light source 101 will be described. The light source 101 is an SLD (Super Luminescent Diode) serving as a representative low-coherence light source. Its wavelength is equal to 830 nm (10-9 m) and its bandwidth is equal to 50 nm. Since the bandwidth exerts an influence on resolution of an optical axial direction of the tomographic image which is obtained, it is an important parameter.

Although the SLD has been selected here as a type of light source, it is sufficient that the low-coherence light can be emitted and an ASE (Amplified Spontaneous Emission) or the like can be also used. As for the wavelength, near-infrared light is suitable in consideration of the measurement of the eye. Further, since the wavelength exerts an influence on resolution in the lateral direction of the tomographic image and the plane image which are obtained, it is desirable to set the wavelength as short as possible and it is set to 830 nm here. Another wavelength may be selected in dependence on a measuring portion of the observation target. The light emitted from the light source 101 is guided to the photocoupler 131 through the single mode fiber 130-1.

Subsequently, the optical path of the reference beam 105 will be described. The reference beam 105 divided by the photocoupler 131 is guided to a lens 135-1 through a single mode fiber 130-2 and is adjusted so as to become a parallel beam of a beam diameter of 4 mm ($10^{-3}$ m). Subsequently, the reference beam 105 is guided to a mirror 114-1 serving as a reference mirror by mirrors 114-2 and 114-3. Since an optical path length of the reference beam 105 has been adjusted so as to be almost equal to an optical path length of the measuring beam 106, the reference beam 105 and the measuring beam 106 can be interfered.

Subsequently, the reference beam 105 is reflected by the mirror 114-1 and is guided to the photocoupler 131 again. Dispersion compensation glass 115 through which the reference beam 105 has passed is provided so that the dispersion at the time when the measuring beam 106 reciprocated the eye 107 to be inspected is compensated for the reference beam 105. A representative value is presumed as a diameter of an average eyeball of Japanese and it is assumed that L1=23 mm.

Further, the electric stage 117-1 can be moved in the direction shown by an arrow and can adjust and control the optical path length of the reference beam 105. The electric stage 117-1 is controlled from the personal computer 125 through an electric stage driver 183 in the driver unit 181.

Subsequently, the optical path (also referred to as irradiating means) of the measuring beam 106 will be described. The measuring beam 106 divided by the photocoupler 131 is guided to a lens 135-4 through the single mode fiber 130-4 and is adjusted so as to become a parallel beam of a beam diameter of 4 mm. The measuring beam 106 passes through the movable beam splitter 161 and the lenses 135-5 and 135-6 and is input to the Y scanner 121-3.

A galvano scanner is used as a Y scanner 121-3 and its driving frequency can be varied within a range up to 500 Hz. The Y scanner 121-3 is driven at 1 Hz when the tomographic image is acquired and it is driven at 30 Hz when the plane image is acquired.

Subsequently, the measuring beam 106 passes through the lens 135-7 and reaches the flip mirror 185-1. The flip mirrors 185-1 and 185-2 are constructed in such a manner that an optical path 186-1 (first optical path) having the X scanner 121-1 and an optical path 186-2 (second optical path) having the X scanner 121-2 can be switched according to an image (plane image or tomographic image) which is obtained. In the case where the flip mirrors 185-1 and 185-2 are controlled so as not to enter the optical path, the optical path 186-1 is used. In the case where the flip mirrors 185-1 and 185-2 are controlled in such a manner that they enter the optical path and the measuring beam is reflected, the optical path 186-2 is used. The operations of the flip mirrors 185-1 and 185-2 are controlled under the personal computer 125.

In the optical path 186-1, the measuring beam 106 passes through the lens 135-8, is input to the X scanner 121-1, passes through the lens 135-9, and reaches the flip mirror 185-2. The optical path 186-1 is used to obtain a tomographic image (OCT image), which will be described hereinafter. A galvano scanner is used as an X scanner 121-1 and its driving frequency can be varied within a range up to 500 Hz. The X scanner 121-1 is driven at 500 Hz when the tomographic image is acquired.

In the optical path 186-2, the measuring beam 106 passes through the lens 135-11, is input to the X scanner 121-2, passes through the lens 135-12, and reaches the flip mirror 185-2. The optical path 186-2 is used to obtain a plane image (SLO image). A resonant scanner is used as an X scanner 121-2 and its driving frequency is set to about 16 kHz. The X scanner 121-2 is driven at 16 kHz when the plane image is acquired.

A center of the measuring beam 106 is adjusted so as to coincide with a rotational center of each of the X scanner 121-1, X scanner 121-2, and Y scanner 121-3. The lenses 135-9, 135-10, and 135-12 are an optical system for scanning a retina 127 and has a role of scanning the retina 127 by the measuring beam 106 while a position near a cornea 126 is set to a fulcrum. All of the focal distances of the lenses 135-9, 135-10, and 135-12 are equal to 50 mm. The electric stage 117-2 can be moved in the direction shown by an arrow and can adjust and control a position of the associated lens 135-10.

By adjusting the position of the lens 135-10, the measuring beam 106 can be converged to a predetermined layer of the retina 127 of the eye 107 to be inspected and can be observed. The apparatus can also cope with a case where the eye 107 to be inspected has a refractive error. When the measuring beam 106 enters the eye 107 to be inspected, it becomes the return beam 108 by the reflection or scattering from the retina 127, is guided to the photocoupler 131 again, and reaches the line camera 139.

A part of the return beam 108 is reflected by the movable beam splitter 161 and is guided to the detector 138 through a lens 135-13. A light blocking plate 172 has a pinhole and has a role of blocking the unnecessary light which is not focused to the retina 127 in the return beam 108. The light blocking plate 172 is conjugately arranged at the focusing position of the lens 135-13. A diameter of the pinhole of the light blocking plate 172 is equal to, for example, 50 micrometers ($10^{-6}$ m). For example, an APD (Avalanche Photo Diode) serving as a photosensor of a high speed and a high sensitivity is used as a detector 138. The electric stage 117-2 is controlled from the personal computer 125 through the electric stage driver 183 in the driver unit 181.

The movable beam splitter 161 can be removed from the optical path under control of the personal computer 125. When the tomographic image is obtained, the movable beam splitter 161 is removed from the optical path and the return beam 108 can be effectively used in order to obtain the tomographic image. Although a spherical lens is used as a lens 135-10 here, a cylindrical lens may be used as a lens 135-10 in dependence on an optical aberration (refractive error) of the eye 107 to be inspected. A new lens may be also added onto the optical path of the measuring beam 106. The cylindrical lens is effective in the case where the eye 107 to be inspected is astigmatic.

The foregoing reference beam 105 and the return beam 108 are combined by the photocoupler 131 and a combined beam is further divided at a ratio of 90:10. A combined beam 142 is spectro-separated every wavelength by the transmission grating 141, is converged by a lens 135-3, and reaches the line camera 139.

Subsequently, a construction of a measuring system in the optical image acquisition apparatus in the embodiment will be described. The optical image acquisition apparatus 100 can obtain the tomographic image (OCT image) constructed by an intensity of an interference signal (interference light) by the Michelson interferometer. The measuring system will be described.

An intensity of the light is converted into a voltage every position (wavelength) by the line camera 139. Specifically speaking, an interference fringe of a spectral region on a wavelength axis is observed on the line camera 139. The obtained voltage signal group is converted into digital values by a frame glover 140 and is data-processed by the personal computer 125, thereby forming the tomographic image. In this instance, the line camera 139 has 1024 pixels and can obtain the intensity every wavelength (1024 division) of the combined beam 142.

The optical image acquisition apparatus 100 can obtain the plane image (SLO image) constructed by the intensity of the return beam 108. The measuring system will be described. A part of the return beam 108 as light which has been reflected or scattered by the retina 127 is reflected by the movable beam splitter 161. After the unnecessary light in the reflected beam was blocked by the light blocking plate 172, the reflected beam reaches the detector 138, and the light intensity is converted into an electric signal. A data process synchronized with the scanning signal is executed to the obtained electric signal by the personal computer 125, so that the plane image is formed.

Subsequently, an obtaining method of the tomographic image (OCT image) by the optical image acquisition apparatus of the embodiment will be described by using FIGS. 2A and 2B.

Figure 3:
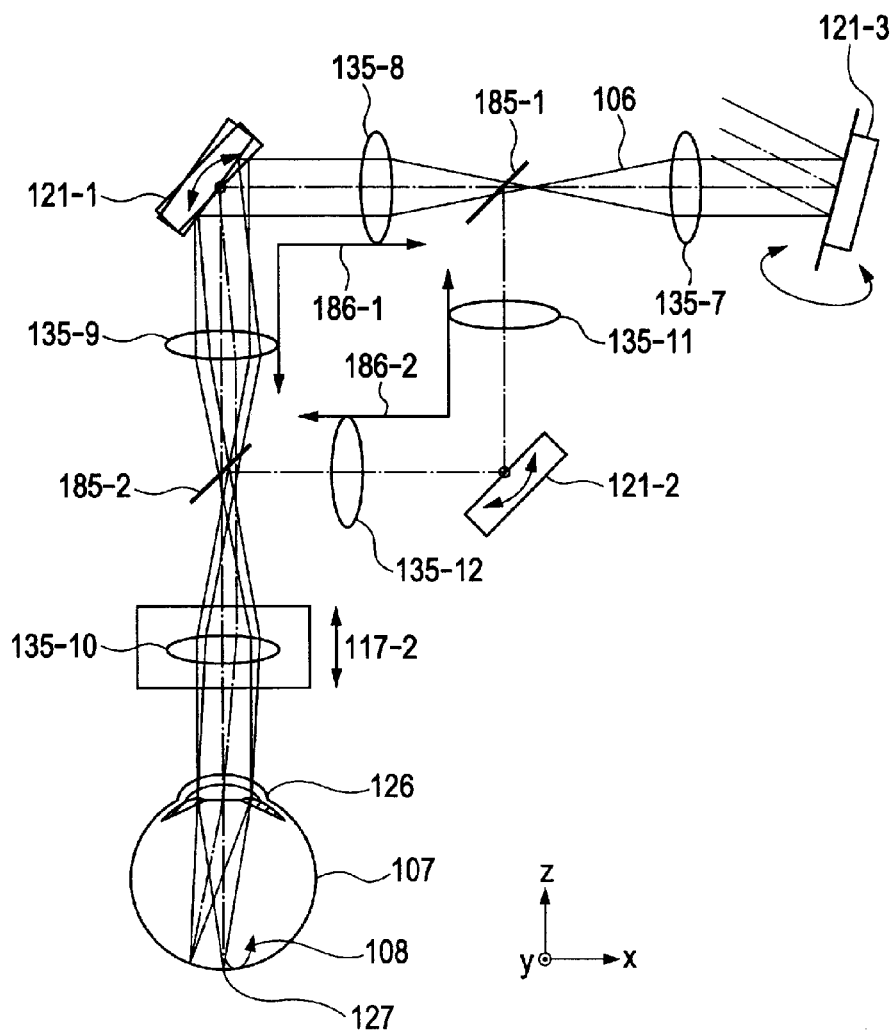
FIG. 3 is a diagram for describing the obtaining method of the image of the optical image acquisition apparatus in the first embodiment of the invention.

The optical image acquisition apparatus 100 controls the X scanner 121-1 and obtains the interference fringe by the line camera 139, so that it can obtain the tomographic image of the retina 127. The flip mirrors 185-1 and 185-2 are controlled so that the measuring beam 106 and the return beam 108 are guided to the optical path 186-1 (FIG. 3). The movable beam splitter 161 is controlled so that the return beam 108 is not guided to the detector 138. The X scanner 121-1, X scanner 121-2, and Y scanner 121-3 are controlled from the personal computer 125 through an optical scanner driver 182 in the driver unit 181 (FIG. 1).

The obtaining method of the tomographic image (surface which is parallel with the optical axis) of the retina 127 will now be described. FIG. 2A is a schematic diagram of the eye 107 to be inspected and illustrates a state where the eye 107 is observed by the optical image acquisition apparatus 100. As illustrated in FIG. 2A, when the measuring beam 106 enters the retina 127 through the cornea 126, it becomes the return beam 108 due to the reflection or scattering at various positions and reaches the line camera 139 with a time delay at each position. Since a band width of the light source 101 is wide and a coherence length is short, when an optical path length of a reference optical path and an optical path length of a measuring optical path are almost equal, the interference fringe can be detected by the line camera 139. As mentioned above, the interference fringe which is obtained by the line camera 139 is the interference fringe in a spectrum region on the wavelength axis.

Subsequently, the interference fringe serving as information on the wavelength axis is converted into an interference fringe on a light frequency axis in consideration of characteristics of the line camera 139 and the transmission grating 141. Further, by inversely Fourier transforming the converted interference fringe on the light frequency axis, information in a depth direction is obtained. Further, as illustrated in FIG. 3, if the interference fringe is detected while driving the X scanner 121-1, the interference fringe is obtained every position of each X axis, that is, the information in the depth direction at every position of each X axis can be obtained. Thus, 2-dimensional distribution of the intensity of the return beam 108 on the XZ surface is obtained, that is, it is a tomographic image 132 (FIG. 2B).

Inherently, as described above, the tomographic image 132 is an image obtained by arranging the intensity of the return beam 108 in an array shape and is displayed, for example, by allocating the intensity to a gray scale. Only a boundary of the obtained tomographic image is emphasized and displayed. Reference numeral 146 denotes a retina pigmented epithelial cells layer and 147 indicates an optical nerve fiber layer.

Subsequently, an obtaining method of the plane image (SLO image) by the optical image acquisition apparatus of the embodiment will be described by using FIG. 2A.

Figure 4:
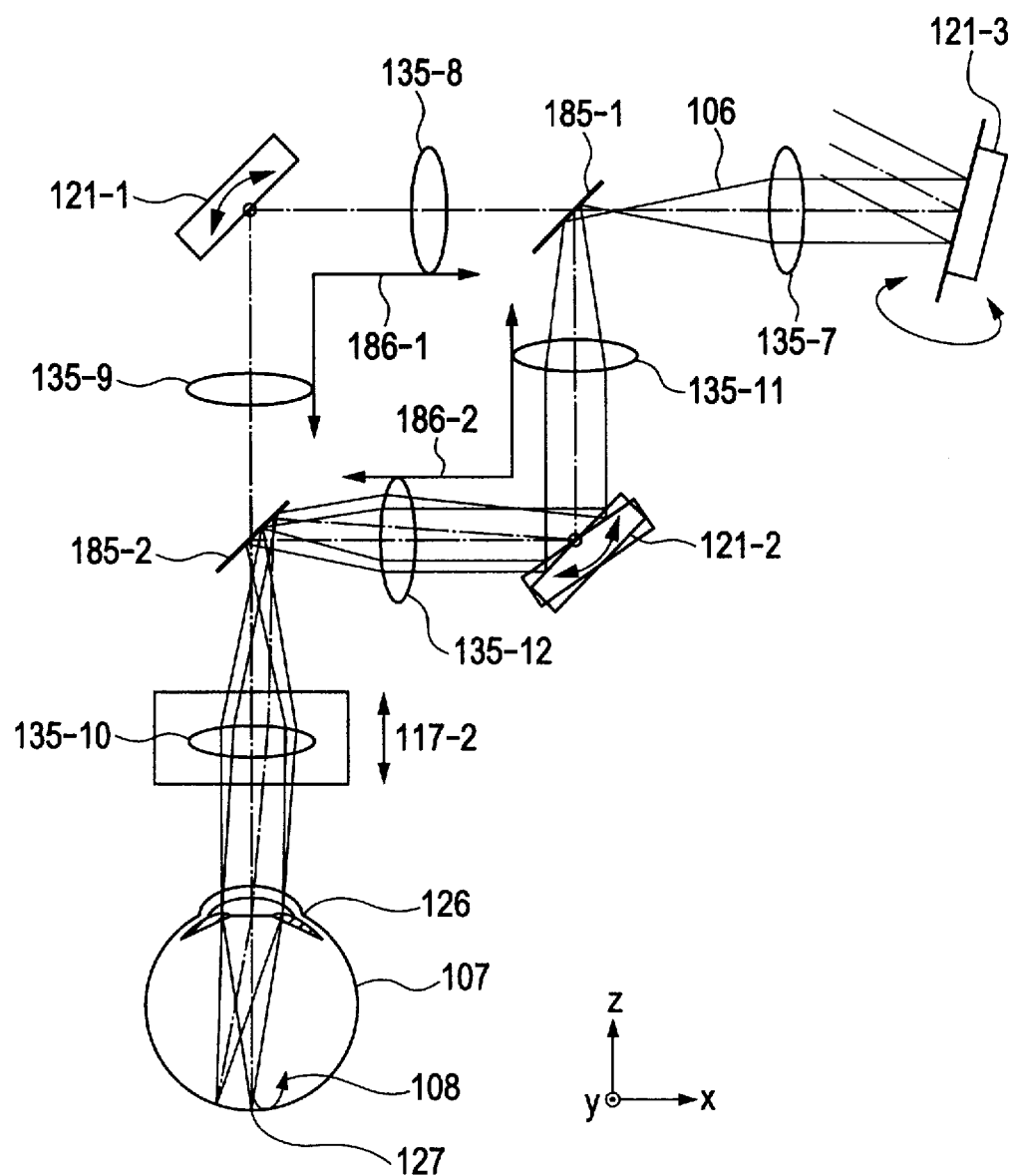
FIG. 4 is a diagram for describing the obtaining method of the image of the optical image acquisition apparatus in the first embodiment of the invention.

The optical image acquisition apparatus 100 controls the X scanner 121-2 and the Y scanner 121-3 and obtains the intensity of the return beam 108 by the detector 138, so that it can obtain the plane image of the retina 127. The flip mirrors 185-1 and 185-2 are controlled so that the measuring beam 106 and the return beam 108 are guided to the optical path 186-2 (FIG. 4). The movable beam splitter 161 is controlled so that the return beam 108 is guided to the detector 138. The X scanner 121-1, X scanner 121-2, and Y scanner 121-3 are controlled from the personal computer 125 through the optical scanner driver 182 in the driver unit 181 (FIG. 1). In this instance, the obtaining method of the plane image (surface which is perpendicular to the optical axis) of the retina 127 will be described here.

Figure 2A:
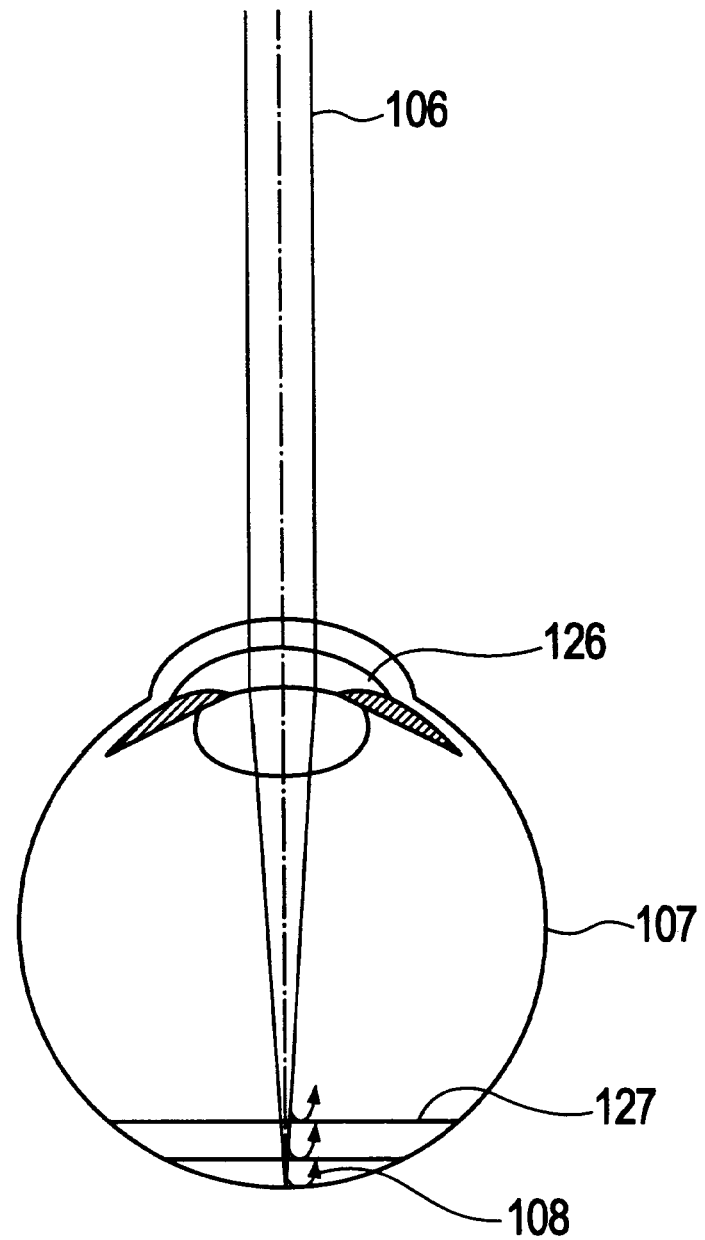
FIG. 2A is a diagram for describing an obtaining method of an image of the optical image acquisition apparatus in the first embodiment of the invention.
Figure 2B:
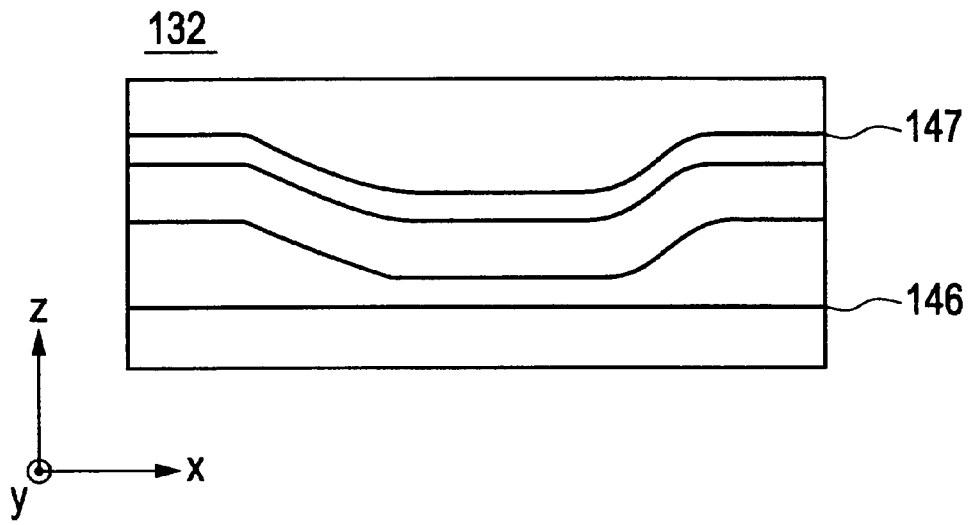
FIG. 2B is a diagram for describing an obtaining method of an image of the optical image acquisition apparatus in the first embodiment of the invention.

FIG. 2A is a schematic diagram of the eye 107 to be inspected and illustrates a state where the eye 107 is observed by the optical image acquisition apparatus 100. As illustrated in FIG. 2A, when the measuring beam 106 enters the retina 127 through the cornea 126, it becomes the return beam 108 due to the reflection or scattering at various positions and reaches the detector 138.

Further, if the intensity of the return beam 108 is detected while driving the X scanner 121-1 as illustrated in FIG. 4, information at every position of each X axis can be obtained. Further, the X scanner 121-2 and the Y scanner 121-3 are simultaneously driven and while raster-scanning the measuring beam 106 to the retina 127, the intensity of the return beam 108 is detected. By the detection, a 2-dimensional distribution of the intensity of the return beam 108 on the XZ surface is obtained, that is, it is the plane image (not shown).

As mentioned above, by constructing the two parallel optical paths by using the two flip mirrors and constructing in such a manner that the optical scanners of different scanning frequencies can be switched and used, each optimum scanning frequency is selected for a desired image of the plane image and the tomographic image and the image acquisition can be performed. Further, since most of the optical system is shared for the objects of the tomographic image acquisition and the plane image acquisition, the image acquisition of the plane image and the tomographic image can be performed by a simple construction. Since the return beam is efficiently guided to the detector or the line camera by using the movable beam splitter on the basis of the image to be acquired, the high-sensitivity image acquisition of the plane image and the tomographic image can be performed. Since the resonant scanner is used as an X scanner to obtain the plane image, the high speed image acquisition can be performed and the plane image without blurring can be obtained.

Second Embodiment

An optical image acquisition apparatus (also referred to as an image acquisition apparatus) according to the second embodiment can obtain at least one of a plane image (SLO image) and a tomographic image (OCT image) of an eye to be inspected as an image of high lateral resolution. Specifically speaking, by using a spatial light modulator provided in an optical system in which an optical system of the SLO for obtaining the plane image and an optical system of the OCT of a Fourier domain optical coherence for obtaining the tomographic image are partially shared, an aberration that is caused in a front eye portion of the eye to be inspected can be corrected. Thus, the good plane image and tomographic image can be obtained irrespective of a diopter or an optical aberration of the eye to be inspected. At this time, it is desirable to obtain the plane image by a small beam diameter (low lateral resolution) at a high speed and to obtain the tomographic image by a large beam diameter at high lateral resolution. It is also desirable to have changing means for changing the beam diameter in accordance with the switching of the image to be obtained. The optical image acquisition apparatus has one X scanner (fourth scanner) and one XY scanner (fifth scanner).

A scanning frequency of the X scanner and a scanning frequency in the X direction of the XY scanner differ. The X scanner and the XY scanner are optically serially arranged. It is a feature that one of the X scanner and the XY scanner is used for scanning in the X direction.

First, a whole schematic construction of the OCT apparatus in the embodiment will be described by using FIG. 5. Since the same component elements as those in the first embodiment in FIG. 1 are designated by the same reference numerals in FIG. 5, the description of the common portions is omitted here.

Figure 5:
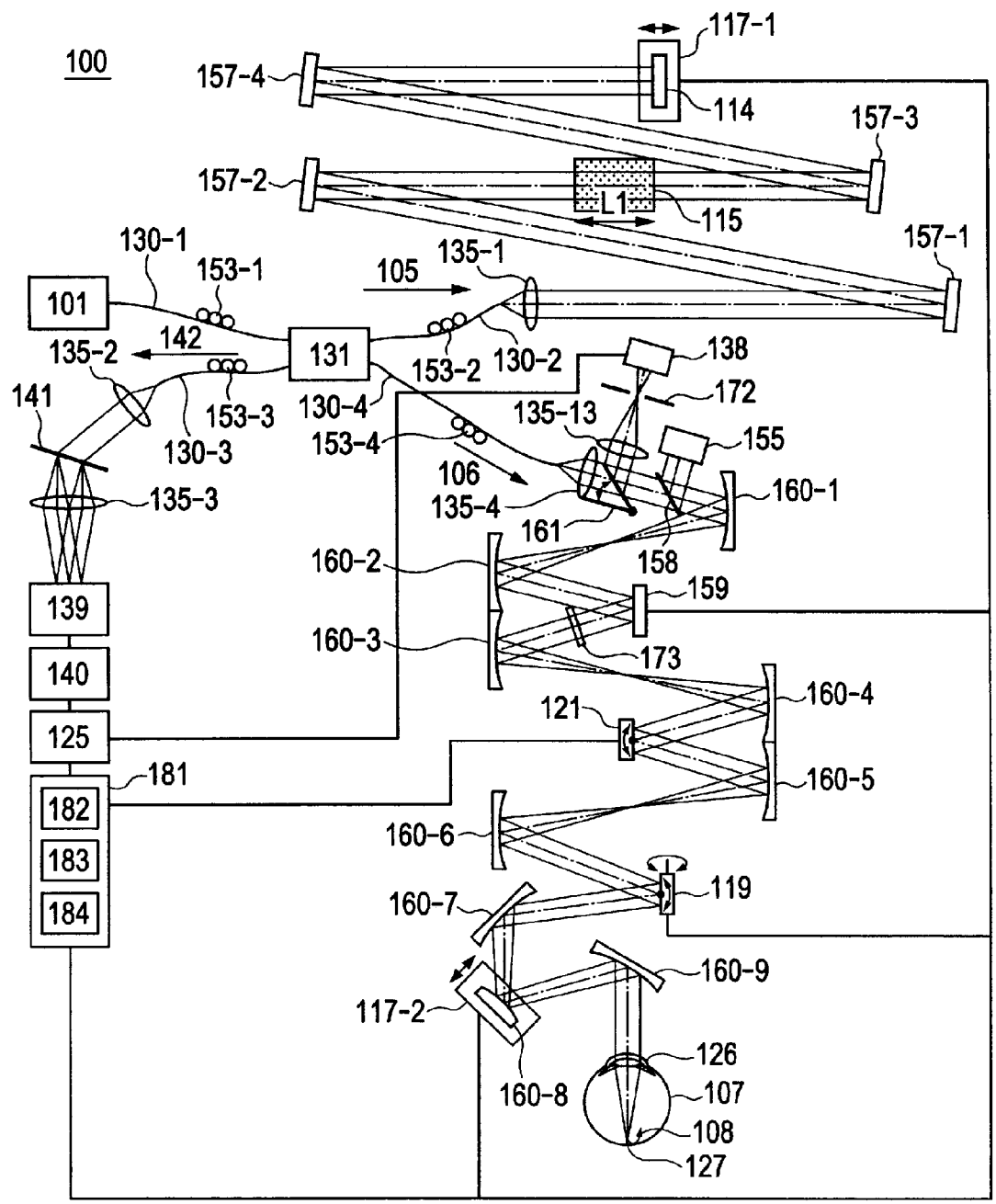
FIG. 5 is a diagram for describing an obtaining method of an image of an optical image acquisition apparatus in the second embodiment of the invention.

In FIG. 5, reference numeral 119 denotes an XY scanner, 155 a wave front sensor, 158 a beam splitter, 159 a spatial light modulator, 160 a spherical mirror, 173 a polarizing plate, and 184 a spatial light modulator driver.

The optical image acquisition apparatus 100 in the embodiment constructs the Michelson interferometer as a whole as illustrated in FIG. 5. In FIG. 5, the measuring beam 106 is guided to the eye 107 to be inspected and serving as an observation target through the single mode fiber 130-4, the spatial light modulator 159, the XY scanner 119, an X scanner 121, spherical mirrors 160-1 to 160-9, and the like. An aberration which the return beam 108 has is measured by the wave front sensor 155. In this instance, the apparatus has a function for reducing the aberration by controlling the spatial light modulator 159 using a liquid crystal, and a good plane image and tomographic image can be obtained irrespective of the diopter and aberration of the eye to be inspected.

Although the whole optical system has been constructed by using a reflective optical system mainly using the spherical mirrors in the embodiment, it can be also constructed by a refractive optical system using lenses in place of the spherical mirrors. Although the reflective spatial light modulator has been used in the embodiment, the whole optical system can be also constructed by using a transmission spatial light modulator. Although the spatial light modulator has been used as a device for correcting the wave front aberration, it is sufficient that the wave front aberration can be corrected, and a variable shape mirror or the like can be also used. Although the XY scanner and the X scanner have optically serially been arranged, a construction in which the two X scanners have optically serially been arranged as mentioned in the first embodiment and a construction in which the aberration is corrected by using the spatial light modulator can be also combined. Since the light source 101 is similar to that in the first embodiment, its description is omitted. The reference beam 105 is guided to a mirror 114 serving as a reference mirror by mirrors 157-1 to 157-4.

Subsequently, the optical path of the measuring beam 106 as a feature of the embodiment will be described. The measuring beam 106 divided by the photocoupler 131 is guided to the lens 135-4 through the single mode fiber 130-4 and is adjusted so as to become a parallel beam of a beam diameter of 4 mm. The polarization controller 153-1 or 153-4 can adjust a polarizing state of the measuring beam 106. Now, the polarizing state of the measuring beam 106 has been adjusted to a linear polarization in the direction which is parallel with the paper surface.

The measuring beam 106 passes through the beam splitter 158 and the movable beam splitter 161, is input to the spatial light modulator 159 through the spherical mirrors 160-1 and 160-2, and is modulated. The spatial light modulator 159 is a modulator for performing the modulation by using the orientation of the liquid crystal, is arranged in such a direction as to modulate a phase of the linear polarization (P polarization) in the direction which is parallel with the paper surface, and is matched with the polarizing direction of the measuring beam 106.

Further, the measuring beam 106 passes through the polarizing plate 173 and is input to the mirror of the X scanner 121 through the spherical mirrors 160-3 and 160-4. Now, the polarizing plate 173 has a role of guiding only the linear polarization light in the direction which is parallel with the paper surface in the return beam 108 to the spatial light modulator 159. The X scanner 121 is an X scanner for scanning the measuring beam 106 in the direction which is parallel with the paper surface. In this instance, a resonant scanner is used and its driving frequency is equal to about 16 kHz. The X scanner 121 is driven at 16 kHz when the plane image is acquired.

Further, the measuring beam 106 is input to a mirror of the XY scanner 119 through the spherical mirrors 160-5 and 160-6. Although the XY scanner 119 has been illustrated as one mirror here, it is actually constructed in such a manner the two mirrors of a mirror for X-scanning and a mirror for Y-scanning are closely arranged.

A center of the measuring beam 106 has been adjusted so as to coincide with a rotational center of the mirror of the XY scanner 119. A driving frequency of the XY scanner 119 can be varied within a range of up to 500 Hz with respect to each axis. The X-scanning mirror is driven at 500 Hz when the tomographic image is acquired. The Y-scanning mirror is driven at 1 Hz when the tomographic image is acquired and it is driven at 30 Hz when the plane image is acquired.

Although the XY scanner 119 has been used as an XY scanner, such a scanner that two axes are scanned by one mirror manufactured by the MEMS technique or the like may be used. Further, the X scanner (sixth scanner) and the Y scanner (seventh scanner) may be separately arranged.

The spherical mirrors 160-7 to 160-9 are an optical system for scanning the retina 127 and has a role of scanning the retina 127 by the measuring beam 106 while a position near the cornea 126 is set to a fulcrum. Although a beam diameter of the measuring beam 106 is equal to 4 mm, the beam diameter may be set to a larger value in order to obtain the tomographic image of the higher resolution. A light power of the measuring beam 106 has been adjusted to 700 microwatts ($10^{-6}$ W) or less so as to cope with the standard regarding safety.

The electric stage 117-2 can be moved in the direction shown by an arrow and can adjust and control the position of the spherical mirror 160-8 serving as an associated spherical mirror. By adjusting the position of the spherical mirror 160-8, the measuring beam 106 can be focused to a predetermined layer of the retina 127 of the eye 107 to be inspected and can be observed. In an initial state, the position of the spherical mirror 160-8 has been adjusted so that the measuring beam 106 enters the cornea 126 in a state of the parallel beam. The apparatus can also cope with a case where the eye 107 to be inspected has a refractive error.

When the measuring beam 106 enters the eye 107 to be inspected, it becomes the return beam 108 by the reflection or scattering from the retina 127, is guided to the photocoupler 131 again, and reaches the line camera 139.

A part of the return beam 108 which is divided by the beam splitter 158 is input to the wave front sensor 155 and the aberration of the return beam 108 is measured. The wave front sensor 155 is a wave front sensor of a Shuck Haltman system. The spherical mirrors 160-1 to 160-9 are arranged so that the XY scanner 119, X scanner 121, cornea 126, wave front sensor 155, and spatial light modulator 159 are optically conjugate. Therefore, the wave front sensor 155 can measure the aberration of the eye 107 to be inspected. The spatial light modulator 159 can correct the aberration of the eye 107 to be inspected. Further, by controlling the spatial light modulator 159 on the basis of the obtained aberration, the aberration which occurs in the eye 107 to be inspected is corrected, thereby enabling the tomographic image of higher lateral resolution to be obtained.

Although the spherical mirror 160-8 has been used here, a cylindrical mirror may be used in place of the spherical mirror 160-8 in dependence on the aberration of the eye 107 to be inspected. A new lens may be added to the optical path of the measuring beam 106. Although the measurement of the aberration using the wave front sensor 155 has been performed by using the measuring beam 106 here, another light source may be used in order to measure the aberration. Another optical path may be constructed in order to measure the aberration. For example, light to measure the aberration can be input from a space between the spherical mirror 160-9 and the cornea 126 by using the beam splitter.

Subsequently, a construction of a measuring system in the optical image acquisition apparatus in the embodiment will be described. Since the construction of the measuring system for measuring the tomographic image (OCT image) and the plane image (SLO image) is similar to that in the first embodiment, its description is omitted.

A part of the return beam 108 which is divided by the beam splitter 158 is input to the wave front sensor 155 and the aberration of the return beam 108 is measured. An image signal obtained by the wave front sensor 155 is input to the personal computer 125 and the aberration is calculated. The obtained aberration is expressed by using a Zernike polynomial and indicates the aberration of the eye 107 to be inspected. The Zernike polynomial is constructed by a term of tilt (inclination), a term of defocus, a term of astigmatism, a term of coma, a term of trifoil, and the like.

Subsequently, the obtaining method of the tomographic image (OCT image) by the optical image acquisition apparatus in the embodiment will be described.

The optical image acquisition apparatus 100 controls the operation of the XY scanner 119, makes the X scanner 121 inoperative, uses it as a fixed mirror, and obtains the interference fringe by the line camera 139, so that it can obtain the tomographic image of the retina 127. The X scanner 121 and the XY scanner 119 are controlled from the personal computer 125 through the optical scanner driver 182 in the driver unit 181 (FIG. 5).

The optical image acquisition apparatus 100 controls the spatial light modulator 159 by using the aberration of the inspection eye 107 measured by the wave front sensor 155 and can obtain the tomographic image while correcting the aberration occurring in the eye 107 to be inspected or the like. The apparatus 100 can also obtain the tomographic image while controlling the spatial light modulator 159 in a real-time manner.

Since the specific obtaining method of the tomographic image is similar to that in the first embodiment, its description is omitted here. In the embodiment, since the aberration occurring in the eye 107 to be inspected is corrected, the tomographic image of the higher lateral resolution and higher contrast as compared with those in the first embodiment can be obtained irrespective of the eye to be inspected.

Subsequently, the obtaining method of the plane image (SLO image) by the optical image acquisition apparatus in the embodiment will be described.

The optical image acquisition apparatus 100 controls the operation only in the Y-axial direction of the XY scanner 119 and the operation of the X scanner 121, fixes the X-axial direction of the XY scanner 119, and obtains the intensity of the return beam 108 by the detector 138, so that it can obtain the plane image of the retina 127. The X scanner 121 and the XY scanner 119 are controlled from the personal computer 125 through the optical scanner driver 182 in the driver unit 181 (FIG. 5).

The optical image acquisition apparatus 100 controls the spatial light modulator 159 by using the aberration of the inspection eye 107 measured by the wave front sensor 155 and can obtain the plane image while correcting the aberration occurring in the eye 107 to be inspected or the like. The apparatus 100 can also obtain the plane image while controlling the spatial light modulator 159 in a real-time manner.

Since the specific obtaining method of the plane image is similar to that in the first embodiment, its description is omitted here. In the embodiment, since the aberration occurring in the eye 107 to be inspected is corrected, the plane image of the higher lateral resolution and higher contrast as compared with those in the first embodiment can be obtained irrespective of the eye to be inspected.

As mentioned above, by constructing the optical path in which a plurality of optical scanners are optically serially arranged and by constructing the apparatus in such a manner that the optical scanners of different scanning frequencies can be switched and used, the optimum scanning frequency is selected for a desired image of the plane image and the tomographic image and the image acquisition can be performed.

Since most of the optical system is shared for the objects of the tomographic image acquisition and the plane image acquisition, the image acquisition of the tomographic image and the plane image can be performed by a simple construction.

Since the measuring beam and the return beam are corrected by using the spatial light modulator when the aberration occurring in the eye to be inspected is corrected, the plane image and the tomographic image of the higher lateral resolution and higher contrast can be obtained.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-027251, filed Feb. 10, 2010, which is hereby incorporated by reference herein in its entirety.

The invention claimed is:
1. An image acquisition apparatus comprising:
an irradiating unit configured to irradiate light from a light source to an inspection object;
a tomographic image obtaining unit configured to obtain a tomographic image of the inspection object on the basis of a combined beam obtained by combining a return beam from the inspection object due to the light irradiated by the irradiating unit and a reference beam corresponding to the light;

a plane image obtaining unit configured to obtain a plane image of the inspection object on the basis of the return beam;

a first scanning unit configured to main-scan the light irradiated by the irradiating unit when the tomographic image is obtained;

a second scanning unit configured to main-scan the light irradiated by the irradiating unit at a speed higher than that in the first scanning unit when the plane image is obtained; and a third scanning unit configured to sub-scan the light irradiated by the irradiating unit when each of the tomographic image and the plane image is obtained.

2. The apparatus according to claim 1, further comprising:
a first separating unit, provided on an optical path of the tomographic image obtaining unit, configured to separate the light from the light source into the beam which is irradiated to the inspection object and the reference beam;

a second separating unit, insertable or removable at a position in front of the first separating unit, configured to separate the return beam; and a control unit configured to control one of the first scanning unit and the second scanning unit in accordance with the insertion or removal of the second separating unit.

3. The apparatus according to claim 2, wherein when the second separating unit has been removed, the tomographic image obtaining unit obtains the tomographic image of the inspection object on the basis of the beam obtained by combining the return beam and the reference beam by the first separating unit, and wherein when the second separating unit has been inserted, the plane image obtaining unit obtains the plane image of the inspection object on the basis of a part of the return beam.

4. The apparatus according to claim 2, wherein the second separating unit is a beam splitter which can be inserted or removed, and wherein the second scanning unit is a resonant scanner.

5. The apparatus according to claim 1, wherein the light source is a single light source for generating low-coherence light, and wherein the single light source is used when each of the tomographic image and the plane image is obtained.

6. The apparatus according to claim 1, further comprising a selecting unit configured to select one of the first scanning unit and the second scanning unit for main-scanning the light irradiated by the irradiating unit, wherein one of the tomographic image and the plane image is selected in accordance with a selection result of the selecting unit.

7. The apparatus according to claim 6, wherein when the first scanning unit is selected by the selecting unit, the tomographic image is obtained, and when the second scanning unit is selected by the selecting unit, the plane image is obtained.

8. The apparatus according to claim 6, wherein the first scanning unit, the second scanning unit, and the third scanning unit are optically serially arranged, wherein when the first scanning unit is selected by the selecting unit, the tomographic image obtaining unit obtains the tomographic image, and wherein when the second scanning unit is selected by the selecting unit, the plane image obtaining unit obtains the plane image.

9. The apparatus according to claim 1, further comprising:
first and second optical paths on which the first scanning unit and the second scanning unit are optically arranged in parallel, respectively; and an optical path selecting unit configured to select one of the first optical path and the second optical path for guiding the light irradiated by the irradiating unit to the inspection object, wherein when the first optical path is selected by the optical path selecting unit, the tomographic image obtaining unit obtains the tomographic image, and when the second optical path is selected by the optical path selecting unit, the plane image obtaining unit obtains the plane image.

10. The apparatus according to claim 9, wherein the optical path selecting unit is a mirror which can be inserted onto or removed from the optical path for guiding the light to the inspection object, and wherein one of the first optical path and the second optical path is selected by the insertion or removal of the mirror.

11. The apparatus according to claim 1, wherein the first scanning unit and the second scanning unit are optically arranged in parallel after the third scanning unit.

12. The apparatus according to claim 1, wherein the inspection object is an eye to be inspected, wherein the tomographic image of the inspection object is a tomographic image of a retina of the eye to be inspected, and wherein the plane image of the inspection object is a fundus image of the eye to be inspected.

13. The apparatus according to claim 1, wherein the third scanning unit operates at a driving speed when the plane image is obtained and at a different driving speed when the tomographic image is obtained.

14. The apparatus according to claim 1, wherein the inspection object comprises an eye to be inspected, and wherein the first, second, and third scanning units are placed at positions optically conjugate with respect to a cornea of the eye to be inspected.

15. The apparatus according to claim 1, wherein the third scanning unit is shared for the obtaining of the tomographic image and for the obtaining of the plane image.

16. An image acquisition apparatus comprising:
a first separating unit configured to separate light from a light source into a measuring beam and a reference beam;

an irradiating unit configured to irradiate the measuring beam separated by the first separating unit to an inspection object;

a second separating unit, insertable or removable at a position in front of the first separating unit, configured to separate a return beam from the inspection object due to the measuring beam irradiated by the irradiating unit;

a tomographic image obtaining unit configured to obtain, when the second separating unit has been removed, a tomographic image of the inspection object on the basis of a beam obtained by combining the return beam and the reference beam by the first separating unit; and a plane image obtaining unit configured to obtain, when the second separating unit has been inserted, a plane image of the inspection object on the basis of a part of the return beam.

17. The apparatus according to claim 13, wherein the light source is a single light source for generating low-coherence light, and wherein the single light source is used when each of the tomographic image and the plane image is obtained.

18. The apparatus according to claim 17, wherein the the light source is controlled to change a light amount in accordance with the insertion or removal of the second separating unit.

19. The apparatus according to claim 18, wherein the tomographic image obtaining unit obtains the tomographic image by controlling the light source to change the light amount to a level smaller than that for the plane image.

20. An image acquisition apparatus comprising:
a measurement unit configured to measure aberration occurring at an inspection object based on a return beam from the inspection object;
a correction unit configured to correct aberration of light based on the aberration measured by the measurement unit;
an irradiating unit configured to irradiate the light corrected by the correction unit to the inspection object;
a tomographic image obtaining unit configured to obtain a tomographic image of the inspection object on the basis of a combined beam obtained by combining a return beam from the inspection object due to the light irradiated by the irradiating unit and a reference beam corresponding to the light; and
a plane image obtaining unit configured to obtain a plane image of the inspection object on the basis of the return beam from the inspection object due to the light irradiated by the irradiating unit.

21. The apparatus according to claim 20, further comprising:
a control unit configured to make switching between the obtainment of the tomographic image by the tomographic image obtaining unit and the obtainment of the plane image by the plane image obtaining unit; and
a change unit configured to change a beam diameter of the light irradiated by the irradiating unit to the inspection object in accordance with the switching made by the control unit.

22. The apparatus according to claim 21, wherein the change unit changes the beam diameter of the light for the tomographic image to a level larger than that for the plane image.

23. A method carried out in an image acquisition apparatus, the image acquisition apparatus obtaining (a) a tomographic image of an inspection object on the basis of a combined beam obtained by combining a return beam from the inspection object due to light irradiated from a light source to the inspection object and a reference beam corresponding to the light, and (b) a plane image of the inspection object on the basis of the return beam, said method comprising:
main-scanning, by controlling a first scanning unit, the light irradiated from the light source to the inspection object when the tomographic image is obtained;
main-scanning, by controlling a second scanning unit, the light irradiated from the light source to the inspection object at a speed higher than that in the first main-scanning when the plane image is obtained; and
sub-scanning, by controlling a third scanning unit, the light irradiated from the light source to the inspection object when each of the tomographic image and the plane image is obtained.

24. The method according to claim 23, wherein the image acquisition apparatus comprises: (a) a first separating unit configured to separate the light from the light source into the beam which is irradiated to the inspection object and the reference beam; and (b) a second separating unit, insertable or removable at a position closer to the inspection object in an optical path of the return beam from the inspection object than to the first separating unit, and
wherein the method further comprises:
controlling one of the first scanning unit and the second scanning unit in accordance with the insertion or removal of the second separating unit in the optical path of the return beam.

25. The method according to claim 24, further comprising:
obtaining the tomographic image of the inspection object on the basis of the beam obtained by combining the return beam and the reference beam by the first separating unit, when the second separating unit has been removed, and
obtaining the plane image of the inspection object on the basis of a part of the return beam, when the second separating unit has been inserted.

26. A non-transitory computer-readable storage medium storing a computer program that causes a computer to execute the method according to claim 23.

27. A method carried out in an image acquisition apparatus, the image acquisition apparatus comprising (a) a first separating unit configured to separate light from a light source into a measuring beam and a reference beam, and (b) a second separating unit, insertable or removable at a position in front of the first separating unit, configured to separate a return beam from the inspection object due to the measuring beam irradiated to the inspection object, wherein the method comprises:
obtaining, when the second separating unit has been removed, a tomographic image of the inspection object on the basis of a beam obtained by combining the return beam and the reference beam by the first separating unit; and
obtaining, when the second separating unit has been inserted, a plane image of the inspection object on the basis of a part of the return beam.

28. A non-transitory computer-readable storage medium storing a computer program that causes a computer to execute the method according to claim 27.

* * * * *